United States Patent [19]

Matier

[11] 4,455,317
[45] Jun. 19, 1984

[54] METHOD FOR TREATING GLAUCOMA BY THE TOPICAL ADMINISTRATION OF SELECTIVELY METABOLIZED BETA-BLOCKING AGENTS

[75] Inventor: William L. Matier, Libertyville, Ill.

[73] Assignee: American Hospital Supply Corporation, Evanston, Ill.

[21] Appl. No.: 276,465

[22] Filed: Jun. 23, 1981

[51] Int. Cl.³ ............................................ A61K 31/24
[52] U.S. Cl. .................................................. 424/309
[58] Field of Search ............... 424/304, 311, 267, 309, 424/300

[56] References Cited

U.S. PATENT DOCUMENTS

| | | |
|---|---|---|
| 3,663,607 | 5/1972 | Barrett et al. ........................ 424/304 |
| 3,740,444 | 6/1973 | Koppe et al. ........................ 424/304 |
| 3,793,365 | 2/1974 | Winter et al. ........................ 562/427 |
| 3,825,583 | 7/1974 | Hussain et al. ........................ 424/311 |
| 3,839,584 | 10/1974 | Hussain et al. ........................ 424/311 |
| 3,868,460 | 2/1975 | Koppe et al. ........................ 424/304 |
| 3,925,446 | 12/1975 | Koppe et al. ........................ 424/267 |
| 4,080,471 | 3/1978 | Carlsson et al. ..................... 424/311 |
| 4,127,674 | 11/1978 | Leopold . | |
| 4,146,638 | 3/1979 | Renth et al. ........................ 424/309 |
| 4,191,765 | 3/1980 | Fritsch et al. ........................ 424/267 |
| 4,195,085 | 3/1980 | Stone . | |

FOREIGN PATENT DOCUMENTS

| | | |
|---|---|---|
| 0003664 | 6/1979 | European Pat. Off. . |
| 41491 | 9/1981 | European Pat. Off. . |
| 41492 | 9/1981 | European Pat. Off. . |
| 2373513 | 11/1978 | France . |

OTHER PUBLICATIONS

The Lancet, Nov. 10, 1979, p. 1028–Ahmad.
J. Am. Med. Assoc., 243, (11), 1131, (1980)–Kohn.
New Eng. J of Med., Mar. 8, 1979, p. 566–Britman.
Drug Therapy, Jul. 1979, pp. 93–94.
Inpharma, Jun. 7, 1980, p. 7–Guzman.
Inpharma, Jul. 12, 1980, pp. 7–8, Kim & Smith and Sando.
Physicians' Desk Reference, Charles E. Baker, Jr., 35th Edition, 1232-1234, (1981).
W. P. Boger, Drugs, 18, 25–32, (1979).
L. Bonomi et al., Glaucoma, Eds. R. Pitts Corck and A. D. S. Caldwell, Academic Press, New York, pp. 99–105, (1980).
Demmler, Forshr. Med. 98, Jg, (1980), Nr. 23, pp. 880–885.
Heel et al., Drugs, 17, 38–55, (1979).
Krieglstein et al., Albrecht v. Graefes Arch. klin. epx. Opthal., 202, 81–86, (1977).
P. Vareilles et al., Investigative Ophthalmology and Visual Science, vol. 16/11, 987, (1977).
T. Zimmerman, Drug Therapy, Jul. 1979, pp. 87–89.
T. J. Zimmerman and W. P. Boger, Surv. Ophthalmol.

Primary Examiner—Douglas W. Robinson
Attorney, Agent, or Firm—Bernard, Rothwell & Brown

[57] ABSTRACT

A method for the treatment of glaucoma or lowering intraocular pressure in a mammal, involving topically administering to the eye of such mammal a selectively metabolized beta-blocking compound of the formula:

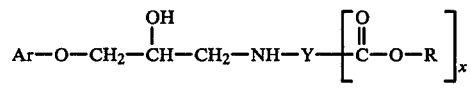

wherein Ar may be substituted or unsubstituted aromatic, Y may be a straight or branched carbon chain or aralkyl, R may be lower alkyl, lower alkenyl, lower alkynyl, aryl, or aralkyl, and x is an integer from 1 to about 3; or a pharmaceutically acceptable salt thereof. Because of a relatively long duration of action of such compounds in ocular fluids and a relatively short duration of action in the systemic circulation, such compounds are useful for the treatment of excessive intraocular pressure without substantial systemic effects.

16 Claims, No Drawings

METHOD FOR TREATING GLAUCOMA BY THE TOPICAL ADMINISTRATION OF SELECTIVELY METABOLIZED BETA-BLOCKING AGENTS

BACKGROUND OF THE INVENTION

The present invention relates to a method for the treatment of glaucoma. More particularly, the invention relates to a novel method of treatment of glaucoma or lowering of intraocular pressure by topically administering beta-adrenergic blocking agents to the eye.

Glaucoma is a condition of the eye characterized by increased intraocular pressure. Untreated, the condition can eventually lead to irreversible retinal damage and blindness. Conventional therapy for glaucoma has involved topical administration of pilocarpine and/or epinephrine, administered to the eye several times daily.

Various beta-blocking agents may also be used to lower intraocular pressure. Such use is described, for example, in reviews by W. P. Boger in *Drugs*, 18, 25-32 (1979) and by T. J. Zimmerman and W. P. Boger in *Survey Ophthmol.*, 23(6), 347 (1979). The use of beta-blockers for the treatment of glaucoma is also described in the patent literature. For example, U.S. Pat. No. 4,195,085 to Stone discloses a method for treatment of glaucoma by the ocular administration of a beta-blocking compound, timolol maleate. U.S. Pat. No. 4,127,674 discloses treating glaucoma with labetalol, a known antagonist of both alpha and beta adrenergic receptors. However, these methods also possess significant drawbacks, in that the absorption of the beta-blocking compound into the systemic circulation can cause undesirable side effects. Such side effects result from prolonged beta-blocking action on the heart, bronchioles and blood vessels. For example, according to *Physicians' Desk Reference*, Charles E. Baker, Jr., 35th Edition, 1981, p. 1233, adverse reactions to the topical use of timolol maleate can include bronchospasm, heart failure, as well as cardiac conduction defects. Accordingly, there is a need for a method of treatment for glaucoma or for lowering intraocular pressure which is relatively free of unwanted systemic side-effects.

Certain beta-blocking agents which contain enzymatically labile ester groups are known to exhibit short-acting beta-blocking effects in the systemic circulation. Such short-acting beta-blocking compounds (SABBs) have been suggested for treatment or prophylaxis of cardiac disorders as a means for reducing heart work or improving rhythmicity for a short duration. Such short-acting beta-blocking compounds avoid the sometimes counterproductive effects of conventional beta-blocking agents, whose effects are long-lived and therefore difficult to precisely control.

SUMMARY OF THE INVENTION

In accordance with the present invention, disclosed herein is a method for the treatment of glaucoma or for lowering intraocular pressure in a mammal, comprising topically administering to the eye of such mammal a beta-blocking compound of the formula:

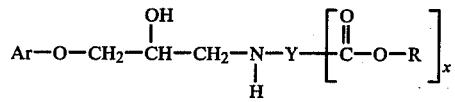

wherein Y is a straight or branched carbon chain of from 1 to about 10 carbon atom or aralkyl of from 8 to about 20 carbon atoms; R is lower alkyl, lower alkenyl, lower alkynyl, aryl or aralkyl; x is an integer from 1 to about 3; Ar is unsubstituted aromatic or aromatic substituted with lower alkyl, lower alkenyl, lower alkynyl, lower alkoxy, halogen, acetamido, amino, nitro, lower alkylamino, hydroxy, lower hydroxyalkyl, acetyl, cyano, or a group of the formula

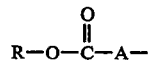

wherein A is a direct bond; lower alkylenyl of from 1 to about 10 carbon atoms; or alkenyl of from 2 to about 10 carbon atoms; or a pharmaceutically acceptable salt thereof.

DETAILED DESCRIPTION OF THE INVENTION

The above-mentioned short-acting beta-blocking compounds have been found to effectively reduce intraocular pressure in the eyes of mammals when topically administered. Because of their short-lived duration of action in the systemic circulation, toxic side-effects produced by their migration out of the eye are consequently reduced. It has further been discovered that certain of these compounds show an increased longevity of effect when present in the ocular fluid compared to the duration of their systemic effects. Consequently, the present invention resides in the treatment of glaucoma or lowering intraocular pressure with a beta-blocking compound which exhibits relatively long duration of action while in the ocular fluid, but which is subject to relatively rapid breakdown into inactive metabolites upon passage to the systemic circulation.

In vitro studies in human whole blood indicate that the ester functions of the compounds used in the method of the invention are subject to enzymatic cleavage. Compounds of the present invention in which the aromatic portion, Ar, is also substituted with an ester-containing group, have two or more potentially labile sites for enzymatic hydrolysis. The time required for substantially complete disappearance of the beta-blocking effects of the compounds of the present invention ranges from about 5-10 minutes to about 1 hour or more in the systemic circulation.

Compounds administered by the method of the present invention are represented by the formula:

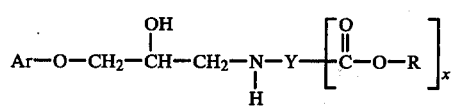

wherein Y may be a straight or branched carbon chain of from 1 to about 10 carbon atoms, e.g., methylene, ethylene, propylene, 2-ethylhexylene, 1,1-dimethylethylene, and the like, or aralkyl of from 8 to about 20 carbon atoms, such as dialkylene phenyl, e.g., 4-ethylenebenzyl, 1-propylene(4-naphthyl)-2-n-butyl, and the like.

R may be lower alkyl of from 1 to about 10 carbon atoms, such as methyl, propy, t-butyl, 3-propylheptyl, and the like; lower alkenyl of from 2 to about 10 carbon atoms, such as ethenyl, propenyl, 4-ethyl-2-hexenyl, and the like, lower alkynyl of from 3 to about 10 carbon atoms, such as propynyl, 4-ethyl-3-octynyl, and the like;

aryl of from 6 to about 10 carbon atoms such as phenyl, 2-tolyl, 2-methoxyphenyl, naphthyl, and the like or aralkyl, wherein the alkyl portion contains from 1 to about 10 carbon atoms and the aryl portion contains from 6 to about 10 carbon atoms, such as benzyl, phenethyl, 1-naphthylpropyl, 3,4-dimethoxyphenethyl, and the like.

The amine substituent may contain one or more ester groups, thus x is an integer from 1 to about 3 provided that when x is greater than 1, different occurrences of the —COOR group may be the same or different.

Ar represents substituted or unsubstituted aromatic, including monocyclic, polycyclic, and heterocyclic ring systems. Aromatic substituents include lower alkyl, of from 1 to about 10 carbon atoms, lower alkenyl of from 2 to about 10 carbon atoms, lower alkynyl, of from 2 to about 10 carbon atoms, lower alkoxy of from 1 to about 10 carbon atoms, halogen, acetamido, amino, nitro, lower alkylamino of from 1 to about 10 carbon atoms, hydroxy, lower hydroxyalkyl of from 1 to about 10 carbon atoms, acetyl, cyano, or a group of the formula

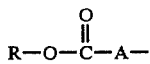

wherein A is a direct bond, lower alkylenyl of from 1 to about 10 carbon atoms, or lower alkenyl of from 2 to about 10 carbon atoms. When two or more groups of the same designation occur in the same formula, those groups are not necessarily identical. The compounds described herein are not limited to any particular stereoisomeric configuration.

In preferred compounds Y is a straight or branched carbon chain of from 1 to about 6 carbon atoms or aralkyl of from 8 to about 12 carbon atoms. Most preferably, Y is a straight or branched carbon chain of from 1 to about 4 carbon atoms. R is preferably lower alkyl of from 1 to about 5 carbon atoms, lower alkenyl of from 2 to about 5 carbon atoms, lower alkynyl of from 3 to about 5 carbon atoms, aryl of from 6 to about 8 carbon atoms, or aralkyl, wherein the alkyl portion contains from 1 to about 5 carbon atoms and the aryl portion contains from 6 to about 10 carbon atoms. Most preferably, R is lower alkyl of from 1 to about 4 carbon atoms or aralkyl, wherein the alkyl portion contains from 1 to about 4 carbon atoms and the aryl portion contains from 6 to about 8 carbon atoms. Particularly preferred R groups are methyl and ethyl. The integer x is preferably 1 or 2; most preferably 1.

Ar is preferably unsubstituted aromatic or aromatic substituted with lower alkyl of from 1 to about 5 carbon atoms, lower alkenyl of from 2 to about 5 carbon atoms, lower alkynyl of from 2 to about 5 carbon atoms, lower alkoxy of from 1 to about 5 carbon atoms, fluoro, chloro, acetamido, amino, nitro, lower alkylamino of from 1 to about 5 carbon atoms, hydroxy, lower hydroxyalkyl of from 1 to about 5 carbon atoms, acetyl, cyano, or a group of the formula

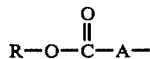

wherein A is a direct bond, alkylenyl of from 1 to about 5 carbon atoms, such as methylene, ethylene, butylene, and the like, or alkenyl of from 2 to about 5 carbon atoms, such as ethenyl, 2-propenyl, 2-butenyl, and the like, and R is lower alkyl of from 1 to about 5 carbon atoms. Most preferably, Ar is 2-alkylphenyl, e.g., 2-methylphenyl; 2-alkoxyphenyl, e.g., 2-methoxyphenyl; or 2-alkoxy carbonylphenyl, e.g., 2-methoxy carbonylphenyl.

The compounds of this invention may be administered as their pharmaceutically acceptable acid addition salts, e.g., as the hydrochloride, sulfate, phosphate, gluconate, tartrate, et cetera.

The beta-blocking compounds used in the present invention along with methods for their preparation are disclosed in co-pending U.S. patent application Ser. No. 211,340, herein incorporated by reference.

The compounds of this invention are advantageously administered topically to the eye in the form of a solution, ointment, or solid insert such as is described in U.S. Pat. No. 4,195,085 to allow controlled or delayed release formulations. Formulations may contain the active compound, preferably, in the form of a soluble acid addition salt, in amounts ranging from about 0.01 to about 10% by wt., preferably, from about 0.5% to about 5% by wt. Unit dosages of the active compound can range from about 0.001 to about 5.0 mg., preferably from about 0.05 to about 2.0 mg. The dosage administered to a patient will depend upon the patient's needs and the particular compounds employed.

Carriers used in the preparations of the present invention are preferably non-toxic pharmaceutical organic or inorganic compositions such as water; mixtures of water and water-miscible solvents, such as lower alcohols; mineral oils; petroleum jellies; ethyl cellulose; polyvinylpyrrolidone and other conventional carriers. In addition, the pharmaceutical preparations may also contain additional components such as emulsifying, preserving, wetting and sterilizing agents. These include polyethylene glycols 200, 300, 400 and 600, carbowaxes 1,000, 1,500, 4,000, 6,000 and 10,000, bacteriocidal components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The method of treatment of this invention advantageously involves the topical administration of eye drops containing the active compound. Formulations for eye drops preferably include the active compound as a soluble acid addition salt in a properly buffered, sterile, aqueous isotonic solution.

The compounds of the present invention are ester group-containing beta-blockers that have a selective, localized, beta-blocking effect in the eye after topical administration. Such compounds are thought to be rapidly metabolized by plasma and/or liver esterases into inactive by-products, upon entering the systemic circulation, and are also thought to be relatively stable in ocular fluids, i.e., lacrimal fluids and aqueous humor.

Consequently, such compounds are useful for the treatment of glaucoma or for lowering intraocular pressure since they remain stable when topically applied to the eye but rapidly metabolize when subsequently absorbed into the systemic circulation.

Some of the compounds break down in the aqueous humor more rapidly than others. Such compounds may advantageously be employed when only a temporary reduction in intraocular pressure is desired, say for diagnostic procedures. Longer-acting compounds are generally used for effecting longer-term reductions in intraocular pressure, such as is desired when treating chronic gluacoma. Thus, the method of the present invention provides a very useful thereapeutic alternative for the treatment of glaucoma or for lowering intraocular pressure.

The present invention is further illustrated by the following examples which are not intended to be limiting.

EXAMPLES I–V

The following compounds were prepared according to the methods disclosed in U.S. patent application Ser. No. 211,340:

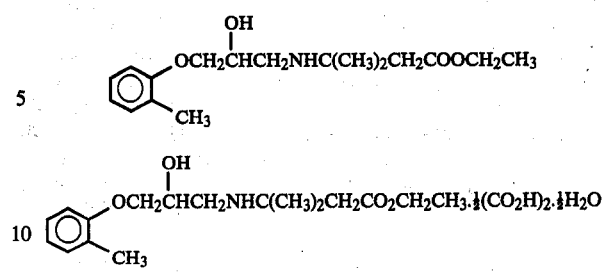

Ethyl 3-(N-Benzyl-amino)3-methylbutyrate Hydrochloride

A mixture of 14 ml (0.1 mole) of ethyl 3,3-dimethylacrylate and 11 ml (0.1 mole) of benzylamine in 50 ml of USP alcohol previously dried over 3 Å molecular sieves, was heated to reflux for five days. The reaction medium was then evaporated under reduced pressure and the resulting oil taken up in 100 ml of ether. The ethereal solution was refrigerated for fifteen hours, filtered and then washed twice with 100 ml portions of water. The ethereal phase was then extracted with 100

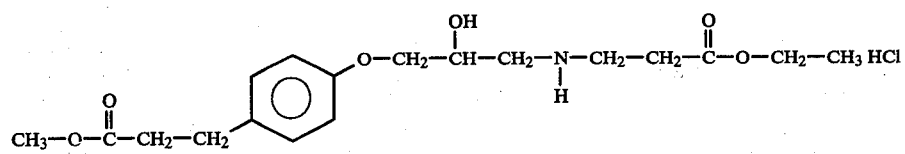

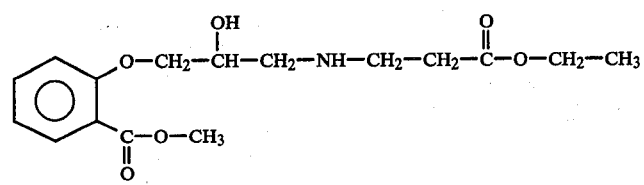

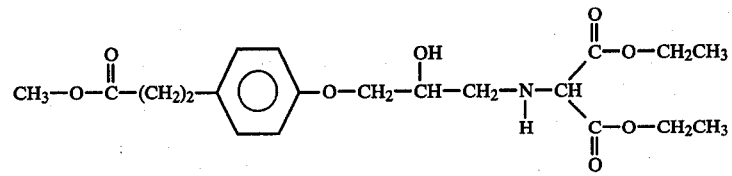

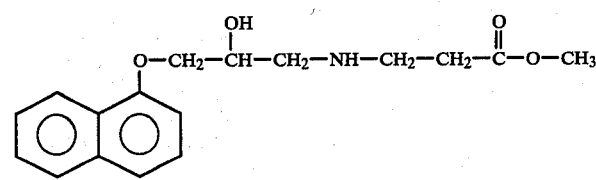

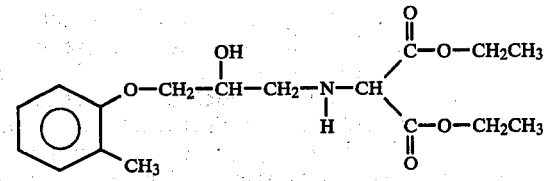

EXAMPLE VI

This example describes procedures for the preparation of compound of the formulas:

ml of 1N HCl. The aqueous extract was washed twice with 100 ml portions of ether and then basified to pH 8 with solid $K_2CO_3$ while under a third 100 ml portion of ether. These phases were separated and the ethereal phase retained and washed once with 100 ml of water. The ethereal solution was dried over $MgSO_4$ and evaporated under reduced pressure to provide a mobile clear oil: NMR (CDCl$_3$) δ1.2 (t, J=7 Hz, 3, —CH$_2$CH$_3$), 1.2 (s, 6, two —CH$_3$), 7.2 (s, 5, Ar). The free amine was converted to its hydrochloride salt by dissolving the oil in 25 ml of reagent alcohol followed by treatment with 75 ml ethereal .Hcl. An additional 200 ml of ether was added and the solution placed in the freezer to effect crystallization. 7.2 gm (31%) of white crystals were obtained: mp 154°–155° C.; NMR (CD$_3$ OD)δ1.2 (t, J+7 Hz, 3, —CH$_2$CH$_3$), 1.5 (s, 6, two —CH$_3$), 7.5 (m, 4, Ar). Analysis Calculated for C$_{14}$H$_{22}$NO$_2$Cl: C. 61.86; H, 8.16; N, 5.15. Found: C, 61.96; H, 8.46; N, 5.00.

Ethyl 3-Amino-3-methylbutyrate Hydrochloride

A mixture of 25 g (0.1 mole) of ethyl 3-(N-benzylamino)-3-methylbutyrate hydrochloride and approximately 2 g of 10% Pd-C in 250 ml of dried USP alcohol was hydrogenated under 55 psi H$_2$ for four days. The reaction medium was then filtered and evaporated under reduced pressure to provide 18 g (100%) of an amber oil which gradually crystallized upon standing: mp 82°–83° C.; NMR (CD$_3$OD) δ1.2 (t, J=7, Hz, 3, —CH$_2$CH$_3$) 1.5 (s, 6, two —CH$_3$), 2.8 (s, 2, —CH$_2$—), 4.2 (q, J=7 Hz, 2, —CH$_2$CH$_3$). Analysis Calculated for C$_7$H$_{16}$NO$_2$Cl: C, 46.28; H, 8.88; N, 7.71. Found: C, 46.46; H, 8.98; N, 7.90.

Ethyl 3-[N[2-Hydroxy-3-(2-methylphenoxy)propyl]amino]-3-methylbutyrate Hemioxalate Hemihydrate A 5 g (0.028 mole) quantity of ethyl 3-amino-3-methylbutyrate hydrochloride was dissolved in 25 ml of water. The aqueous solution was placed under 50 ml of ethyl acetate and then basified to pH 8 with solid K$_2$CO$_3$. The phases were separated and the aqueous layer extracted two additional times with 50 ml portions of ethyl acetate. The combined organic phase was dried over 5 g of MgSO$_4$ and then evaporated under reduced pressure with temperature not exceeding 55° C. The free amine was obtained as a clear oil: 3.1 g (75%; 0.021 mole); NMR (CD$_3$OD) δ1.1 (s, 6, two —CH$_3$), 1.2 (t, J=7 Hz, 3, —CH$_2$CH$_3$), 2.4 (s, 2, —CH$_2$—), 4.1 (q, J=7 Hz, 2, —CH$_2$CH$_3$). The free amine was then taken up in 25 ml of USP alcohol previously dried over 3 Å molecular sieves, and combined with 3.4 g (0.021 mole) of 1-(2-methylphenoxy)-2,3-epoxypropane.

The resulting solution was heated to reflux for six hours. The reaction medium was then evaporated under reduced pressure to an oil which was taken up in 25 ml portions of water. The ethereal phase was then extracted with 25 ml portions of water. The ethereal phase was then extracted with 25 ml of 1N HCl. The aqueous acid solution was washed with two 25 ml portions of ether and then basified to pH 8 with solid K$_2$CO$_3$ while under a third 50 ml portion of ether. The ethereal phase was separated, washed with 25 ml of water, dried over MgSO$_4$ and evaporated under reduced pressure. 2.2 g (0.007 mole) of this free amine was thus obtained as a faintly yellow oil. The oil was taken up in 10 ml of acetone and added dropwise to a solution of 0.9 g (0.007 mole) of oxalic acid dihydrate in 15 ml acetone. This solution was placed in a freezer to effect crystallization. An initial, small crop of crystals was obtained which did not agree within±0.4% of the theoretical elemental analysis. A second, larger crop, 1 g (14%) was then obtained from the mother liquor after returning to the freezer: mp 127°–128° C.; NMR (CD$_3$OD) δ1.3 (t, J=7 Hz, 3, —CH$_2$CH$_3$), 1.5 (s, 6, two —CH$_3$), 2.2 (s, 3, Ar —CH$_3$), 7 (m, 4, Ar). Analysis Calculated for C$_{18}$H$_{28}$NO$_6$.½H$_2$O: C, 59.48; H, 8.04; N, 3.86. Found: C, 59.56; H, 8.03; N, 3.60. Beta-Blocking Activity in vitro: PA$_2$=8.6 (atria).

EXAMPLE VII

This example describes the synthesis of a compound of the formula:

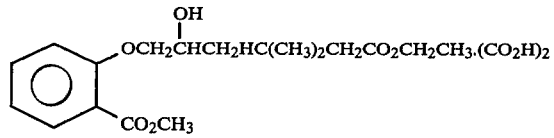

Ethyl 3-[N-[2-Hydroxy-3-[2-(methoxycarbonyl)phenoxy]-propyl]amino]-3-methylbutyrate Oxalate A mixture of 4 g (0.028 mole) of ethyl 3-amino-3-methylbutyrate free amine and 3.8 g (0.018 mole) of ethyl 2-(2,3-epoxypropoxy)benzoate in 50 ml of isopropylalcohol was heated to reflux for six hours. The reaction medium was then evaporated under reduced pressure to provide an oil which was taken up in 50 ml of ether. The ethereal solution was washed five times with 50 ml portions of water, dried over MgSO$_4$ and then evaporated under reduced pressure. 2.4 g (0.007 mole) of a faint yellow oil was obtained and taken up in 15 ml of acetone. The acetone solution was added dropwise to 0.9 g (0.007 mole) of oxalic acid dihydrate in 25 ml of acetone. This solution was treated with 50 ml of ether and crystallization occurred after refrigeration to provide 1.8 g (23%) of white crystalline clusters: mp 96°–98° C.; NMR (CD$_3$OD) δ1.1 (t, J=7 Hz, 3, —CH$_2$CH$_3$), 1.5 (s, 6, two —CH$_3$) 3.8 (s, 3, —CO$_2$CH$_3$), 7.4 (m, 4, Ar); Analysis Calculated for C$_{20}$H$_{29}$NO$_{10}$: C, 54.17; H, 6.59; N, 3.16. Found: C, 54.33; H, 6.87; N, 2.91. Beta-blocking Activity in vitro: PA$_2$=7.8 (atria). In vivo Duration of action: 5 min. (180 min infusion) (80% recovery time). Potency: 5.0 mg/kg/180 min.

EXAMPLE VIII

The intraocular pressure lowering effect of the compounds described in Examples I–VII are demonstrated in rabbits with normotensive eyes.

Sterile, isotonic saline solutions of each of the compounds used in procedures of Examples I to VII are prepared by dissolving 10, 30 and 100 mg samples of each of the active compounds in 1 ml of saline to give 1%, 3% and 10% solutions with pH about 6.0–7.0. Free amines require one equivalent of HCl to effect dissolution.

The intraocular pressure lowering effect of each compound is determined by treating the eyes of healthy rabbits with the above solutions. Three rabbits are used to evaluate the effect of each drug concentration. A standard dose of 50 μl of each drug solution is applied to one eye of each of the three rabbits. Intraocular pressure of both eyes is measured with a pressure tonograph of a Mackay-Marg Tonometer before drug administration and at 15, 30, 45, 60, 120, 180, 240, 300, 360, 420 and 480 min. after dosing. Control rabbits are treated similarly with sterile isotonic saline solution. Intraocular pressure lowering in the treated eyes is compared with the untreated eyes, with saline treated eyes and with predrug pressures. Each of the compounds tested exhibits intraocular pressure-lowering activity.

EXAMPLE IX

The experiment of Example VIII is repeated in all essential details, except that rabbits which have cortuosteroid induced ocular hypertension, as described by Bonomi, L., et al. *Glaucoma,* Eds. R. Pittscrick, A. D. S. Caldwell, Academic Press, New York, pp. 99-107 (1980), are substituted for the normotensive rabbits. Each of the test compounds exhibits intraocular pressure-lowering activity in this model.

We claim:

1. A method for treating glaucoma or for lowering intraocular pressure in a mammal, which comprises topically applying to the eye of such mammal an intraocular pressure-lowering effective amount of a compound represented by the formula:

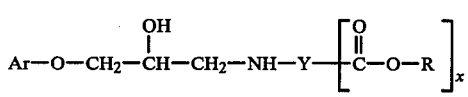

wherein Y is a straight or branched carbon chain of from 1 to about 10 carbon atoms or aralkyl of from 8 to about 20 carbon atoms; R is lower alkyl of from 1 to about 10 carbon atoms, lower alkenyl of from 2 to about 10 carbon atoms, lower alkynyl of from 3 to about 10 carbon atoms; x is an integer from 1 to about 3; Ar is phenyl or napthyl optionally additionally substituted with lower alkyl of from 1 to about 10 carbon atoms, lower alkenyl of from 2 to about 10 carbon atoms, lower alkynyl of from 2 to about 10 carbon atoms, lower alkoxy of from 1 to about 10 carbon atoms, halogen, or a group of the formula

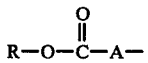

wherein A is a direct bond, lower alkylene of from 1 to about 10 carbon atoms, or lower alkenylene of from 2 to about 10 carbon atoms; or a pharmaceutically acceptable salt thereof.

2. The method of claim 1, wherein Y is a straight or branched carbon chain of from 1 to about 6 carbon atoms or aralkyl of from 8 to about 12 carbon atoms and R is lower alkyl of from 1 to about 5 carbon atoms, lower alkenyl of from 2 to about 15 carbon atoms, lower alkynyl of from 3 to about 5 carbon atoms.

3. The method of claim 2 wherein Ar is unsubstituted aromatic or aromatic substituted with lower alkyl of from 1 to about 5 carbon atoms, lower alkenyl of from 2 to about 5 carbon atoms, lower alkoxy of from 1 to about 5 carbon atoms, fluoro, chloro, or a group of the formula

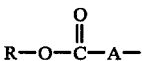

wherein A is a direct bond, alkylene of from 1 to about 5 carbon atoms, or alkenylene of from 2 to about 5 carbon atoms.

4. The method of claim 3, wherein Y is a straight or branched carbon chain of from 1 to about 4 carbon atoms and R is lower alkyl of from 1 to about 4 carbon atoms, and x is 1 or 2.

5. The method of claim 4 wherein Ar is unsubstituted phenyl or phenyl substituted with lower alkyl of from 1 to about 5 carbon atoms, fluoro, chloro, methoxy, ethoxy or a group of the formula

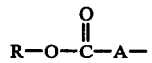

wherein A is alkylene of from 1 to about 5 carbon atoms, or alkenylene of from 2 to about 5 carbon atoms and x is 1.

6. The method of claim 4 wherein Ar is phenyl, 2-methylphenyl, or 2-ethoxyphenyl and x is 1.

7. The method of claim 6 wherein R is methyl or ethyl.

8. The method of claim 1 wherein the topically applied compound is

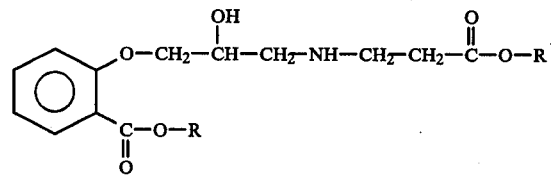

wherein R is methyl or ethyl; or a pharmaceutically acceptable salt thereof.

9. The method of claim 1 wherein the topically applied compound is

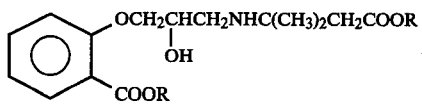

wherein R is methyl or ethyl; or a pharmaceutically acceptable salt thereof.

10. The method of claim 1 wherein the topically applied compound is

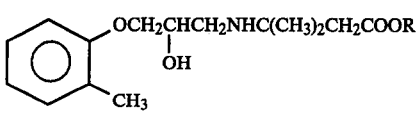

wherein R is methyl or ethyl; or a pharmaceutically acceptable salt thereof.

11. The method of claim 1, 2, 3, 4, 5, 6, 7, 8, 9, or 10 wherein the topically applied compound is a hydrochloride, sulfate, phosphate, gluconate or tartrate acid addition salt.

12. The method of claim 1, 2, 3, 4, 5, 6, 7, 8, 9 or 10, wherein the compound is administered as a solution of about 0.01% to about 10% by weight of the active ingredient in an opthalmologically acceptable carrier.

13. The method of claim 7 wherein the compound is administered as a solution of about 0.5% to about 5% by weight of the the active ingredients in an ophthalmologically acceptable carrier.

14. The method of claim 1, 2, 3, 4, 5, 6, 7, 8, 9 or 10 wherein the unit dosage of the active compound ranges from about 0.001 mg to about 5.0 mg.

15. The method of claim 9 wherein the unit dosage of the active compound ranges from about 0.05 mg to about 2.0 mg.

16. The method of claim 1, 2, 3, 4, 5, 6, 7, 8, 9, or 10 wherein the active compound is contained in a sterile, aqueous, buffered, isotonic solution.

* * * * *

UNITED STATES PATENT AND TRADEMARK OFFICE
CERTIFICATE OF CORRECTION

PATENT NO. : 4,455,317
DATED : June 19, 1984
INVENTOR(S) : Matier

It is certified that error appears in the above-identified patent and that said Letters Patent is hereby corrected as shown below:

Column 9, claim 2, line 47, "15" should be "5"

Signed and Sealed this

Nineteenth Day of March 1985

[SEAL]

Attest:

DONALD J. QUIGG

*Attesting Officer*     *Acting Commissioner of Patents and Trademarks*